US00PP09066P

United States Patent [19]

Jacobsen

[11] Patent Number: Plant 9,066

[45] Date of Patent: Feb. 28, 1995

[54] POINSETTIA PLANT 'PJ 3112'

[75] Inventor: Peter Jacobsen, Skibby, Denmark

[73] Assignee: Paul Ecke Ranch, Encinitas, Calif.

[21] Appl. No.: 192,441

[22] Filed: Feb. 7, 1994

[51] Int. Cl.[6] ..... A01H 5/00

[52] U.S. Cl. ..... Plt./86.4

[58] Field of Search ..... Plt. 86.4

[56] References Cited

PUBLICATIONS

Sigurbjornsson, B., "Chapter 8 Induced Mutations" *Crop Breeding* 1983, American Society of Agronomy and Crop Science Society of America, pp. 153–176.

*Primary Examiner*—James R. Feyrer

*Attorney, Agent, or Firm*—Arnold, White & Durkee

[57] ABSTRACT

Poinsettia 'PJ 3112' is a new cultivar, distinguished by bright orange-red bracts and intense dark green foliage with self-branching characteristics. 'PJ 3112' is a color sport of the dark red bracted 'Lilo' (U.S. Plant Pat. No. 6,694) with the same early flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as an induced orange-red bracted sport of 'Lilo' (U.S. Plant Pat. No. 6,694) in my greenhouse in Skibby, Denmark. It was induced through irradiation of vegetative plants with 2500 rads of gamma radiation, randomly applied to the whole plant. A single plant from the irradiated group exhibited orange-red flower bracts. The mutant was characterized by its self-branching, orange-red flower bracts and dark green foliage, traits which help distinguish it from other poinsettia cultivars, and seem to make it a desirable plant for commercial greenhouse production. No other similar plants were observed from the irradiation nor were any other changes in the plant observed which would appear to have commercial merit. 'PJ 3112' differed from its patent 'Lilo' in having bright, orange-red bracts as compared to the dark red bracts of 'Lilo', but otherwise had characteristics similar to the parent.

After selection 'PJ 3112' was vegatatively reproduced from stem cuttings for test purposes in Encinitas, Calif. Tip cuttings were made from the new plant over 3–5 generations. By subjecting clones of this plant to successive generations of vegetative propagation, it was demonstrated that the distinctive characteristics of 'PJ 3112' held true from generation to generation. The observed characteristics were stable and not apparently due to chemical treatment, cultural conditions or disease. Reversion was not observed thus indicating that the characteristics of the new plant were genetically determined.

DESCRIPTION OF THE PHOTOGRAPHS

Poinsettia 'PJ 3112' is illustrated in the accompanying color photographs. The upper photo is a side view of 3 single stem plants per pot in full flower. The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of 'Lilo' (U.S. Plant Pat. No. 6,694), induced through irradiation of vegetative plants with 2500 rads of gamma radiation.

Classification:

*Botanic.*—*Euphorbia pulcherrima* Willd.

*Common name.*—Poinsettia.

*Cultivar name.*—'PJ 3112'.

Form: Shrub.

Height: Medium.

Growth habit: As a single stemmed plant, upright and vigorous with self-branching side shoots. The application of a chemical growth retardant may be needed to restrict height for commercial pot plant production. I observed 3 unpinched plants in a pot with an overall height of 52 cm. and an overall width of 53 cm. The bract diameter of individual flowers were 33 cm.

Branching: Axillary branches will develop and terminate in a flower without pinching. However, it is usually desirable to pinch 'PJ 3112' before flower induction and remove all terminal dominance. Then, all axillary branches will develop uniformly and at a faster rate.

Growth rate: Rooting of stem cutting occurs in 12–18 days under intermittent mist.

Flowering: The plant will flower in about eight to nine weeks under continuous long night conditions and night temperatures of about 16–18 degrees C. Like its parent, ('Lilo'), 'PJ 3312' will be in full bloom in late November in the northern hemisphere under natural daylength conditions.

Foliage: At flowering, plants were observed with about 22 uniformly dark green leaves, one leaf per node. The leaves were of medium size, leaf blades typically being 12–14 cm. long and 10–11 cm. wide with leaf petioles 7–8 cm. long.

*Leaf shape.*—Typical leaves are generally ovate with obtuse bases and acuminate tips. Leaf margins are entire or slightly lobed with 1 or 2 indentations on each side of the leaf blade.

*Color.*—Upper side — Dark green, darker than RHS 147A. Under side — Green, near RHS 147B.

Bracts: Generally there were 30–33 orange-red bracts of various sizes subtending the cyathia. The primary bracts are large, have blades typically 14–15 cm. long and 10–11 cm. wide with petioles 4 cm. long.

*Shape.*—Primary bracts are ovate with acute bases and acuminate tips and weakly lobed with 1 small indentation on either side of the bract. Secondary bracts are elliptic and have entire margins.

*Color.*—Upper side — Bright orange-red, 42B (having a brightness that may give a perception of 45A-B in certain light conditions). Under side — Orange-red, between RHS 45C-D.

Flowers: Generally, 33 cyathia (flowers) were present when the plant was in full bloom. Each cyanthium is about 7 mm long and 6 mm wide, green in color, and fringed with red at the distal end. A yellow nectar cup protrudes from the side of each cyathium. The flower pedicel is also green and about 3 mm in length. The stamens protruding from the cyathia are dark red. The anthers are bifurcate; the pollen is yellow and copious. The stigmas are dark red and trifucate. Cyathia retention was about three weeks beyond the time the flower was fully mature.

*Nectar exudate.*—Present, abundant.

*Seed formation.*—Self-incompatible.

*Fertility.*—Not observed.

Post production: 'PJ 3112' is resistant to epinasty after being confined to shipping containers and recovers rapidly if the plant does become epinastic. The foliage and bract retetion is excellent even under low light intensities in the consumer's home.

What is claimed is:

1. A new and distinct Poinsettia cultivar, substantially as herein shown an described, distinguished by its intense dark green foliage, bright orange-red bracts, self branching and good leaf and bract retention in the consumer environment.

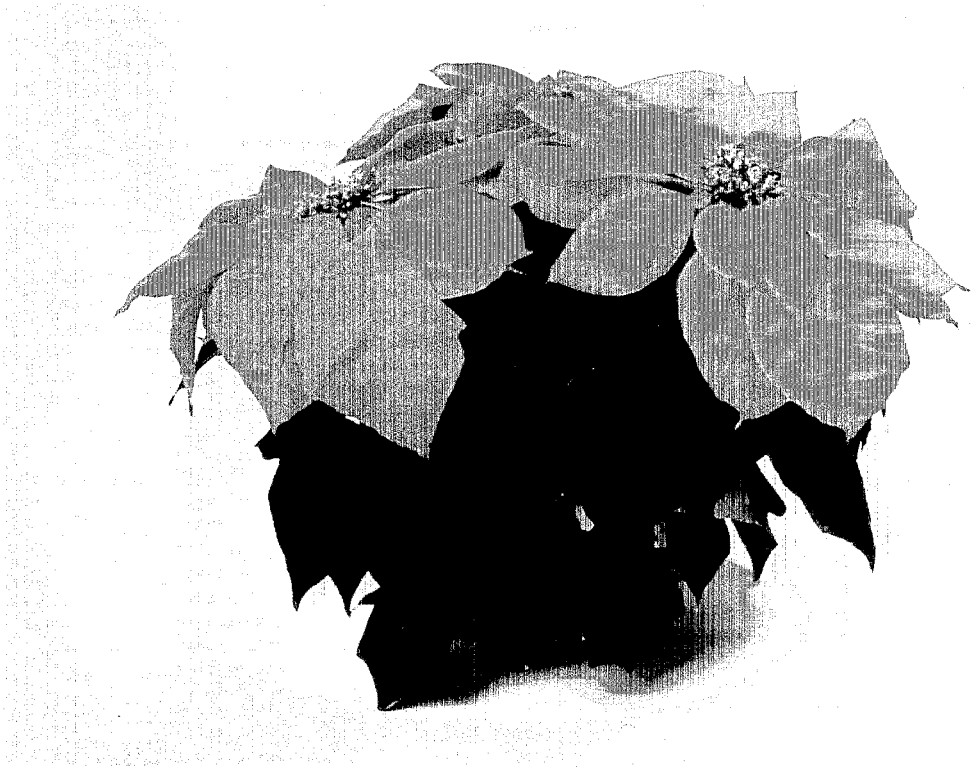
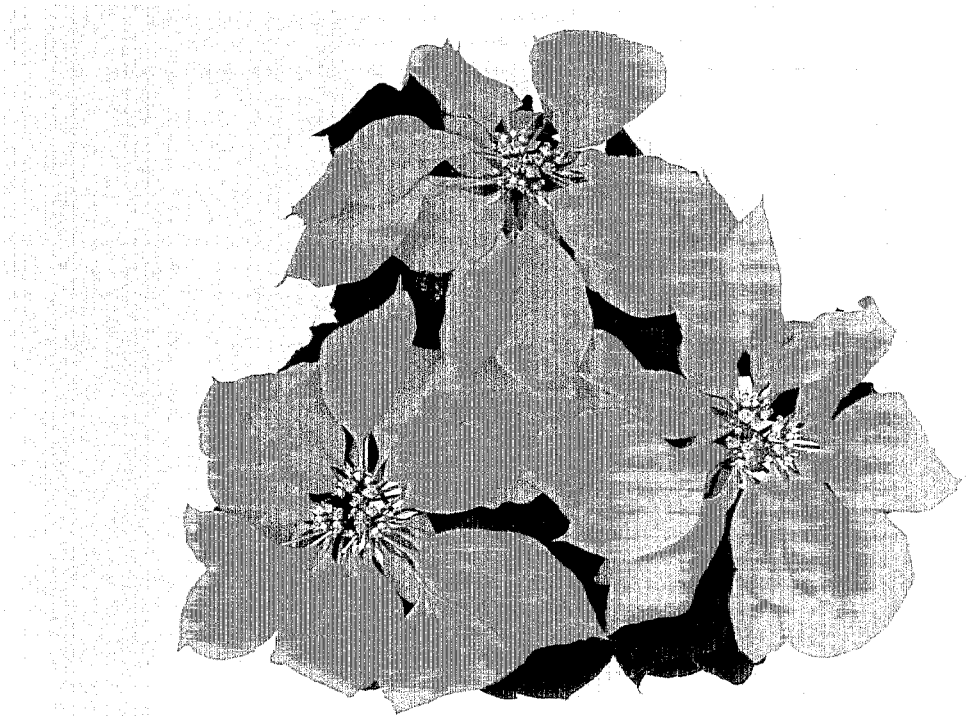

* * * * *